US010052162B2

(12) United States Patent
Bai et al.

(10) Patent No.: US 10,052,162 B2
(45) Date of Patent: Aug. 21, 2018

(54) MEDICAL IMAGING SYSTEM FOR ILLUMINATING TISSUE SAMPLES USING THREE-DIMENSIONAL STRUCTURED ILLUMINATION MICROSCOPY

(71) Applicants: Yanhui Bai, Toronto (CA); Michael Frank Gunter Wood, Toronto (CA); Siu Wai Jacky Mak, Toronto (CA); Murugathas Yuwaraj, Toronto (CA); Alexander Gyles Panther, Toronto (CA); Sean Jy-Shyang Chen, Toronto (CA)

(72) Inventors: Yanhui Bai, Toronto (CA); Michael Frank Gunter Wood, Toronto (CA); Siu Wai Jacky Mak, Toronto (CA); Murugathas Yuwaraj, Toronto (CA); Alexander Gyles Panther, Toronto (CA); Sean Jy-Shyang Chen, Toronto (CA)

(73) Assignee: SYNAPTIVE MEDICAL (BARBADOS) INC., Bridgetown (BB)

(*) Notice: Subject to any disclaimer, the term of this patent is extended or adjusted under 35 U.S.C. 154(b) by 0 days.

(21) Appl. No.: 15/035,295

(22) PCT Filed: Aug. 24, 2015

(86) PCT No.: PCT/IB2015/056405
§ 371 (c)(1),
(2) Date: May 9, 2016

(87) PCT Pub. No.: WO2017/033043
PCT Pub. Date: Mar. 2, 2017

(65) Prior Publication Data
US 2017/0258528 A1 Sep. 14, 2017

(51) Int. Cl.
A61B 34/20 (2016.01)
A61B 1/06 (2006.01)
(Continued)

(52) U.S. Cl.
CPC .......... *A61B 34/20* (2016.02); *A61B 1/00045* (2013.01); *A61B 1/05* (2013.01);
(Continued)

(58) Field of Classification Search
CPC ....... A61B 34/20; A61B 1/00045; A61B 1/05; A61B 1/06; G02B 21/0012;
(Continued)

(56) References Cited

U.S. PATENT DOCUMENTS 4,495,516 A 1/1985 Moore et al.
5,098,426 A 3/1992 Sklar et al.
(Continued)

FOREIGN PATENT DOCUMENTS

EP 2444833 A1 4/2012
EP 2469294 A1 6/2012

OTHER PUBLICATIONS

Lin Shaq et al., "Super-resolution 3D microscopy of live whole cells using structured illumination", Nature Methods, 8, Oct. 16, 2011, pp. 1044-1046.
(Continued)

Primary Examiner — Nguyen Truong
(74) Attorney, Agent, or Firm — Perry+Currier Inc.

(57) ABSTRACT

A medical imaging system for illuminating tissue samples using three-dimensional structured illumination microscopy is port-based surgery is provided. The system comprises: an image sensor; a mirror device; zoom optics; a light modulator; a processor; and collimating optics configured to convey one or more images from the modulator to the mirror, the mirror configured to convey the images to the
(Continued)

zoom optics, the zoom optics configured: to convey the image(s) from the mirror to a tissue sample; and convey one or more resulting images, formed by the image(s) illuminating the sample, back to the mirror, which conveys the resulting image(s) from the zoom optics to the image sensor, and, the processor configured to control the modulator to form the image(s), the image(s) including at least one pattern selected to interact with the sample to generate different depth information in each of resulting image(s).

16 Claims, 9 Drawing Sheets

(51) Int. Cl.
| | |
|---|---|
| *A61B 1/05* | (2006.01) |
| *A61B 1/00* | (2006.01) |
| *H04N 13/02* | (2006.01) |
| *H04N 5/335* | (2011.01) |
| *G02B 21/00* | (2006.01) |
| *G02B 27/30* | (2006.01) |
| *G02B 21/02* | (2006.01) |
| *G02B 21/04* | (2006.01) |
| *G02B 21/06* | (2006.01) |
| *G02B 21/36* | (2006.01) |
| *G02B 23/24* | (2006.01) |

(52) U.S. Cl.
CPC ............. *A61B 1/06* (2013.01); *G02B 21/008* (2013.01); *G02B 21/0012* (2013.01); *G02B 21/0052* (2013.01); *G02B 21/0064* (2013.01); *G02B 21/025* (2013.01); *G02B 21/04* (2013.01); *G02B 21/06* (2013.01); *G02B 21/361* (2013.01); *G02B 23/2415* (2013.01); *G02B 23/2484* (2013.01); *G02B 27/30* (2013.01); *H04N 5/335* (2013.01); *H04N 13/0253* (2013.01); *A61B 1/00188* (2013.01); *A61B 2034/2055* (2016.02)

(58) Field of Classification Search
CPC ............ G02B 21/0052; G02B 21/0064; G02B 21/008; G02B 21/025; G02B 21/04; G02B 21/06
USPC .......................................................... 348/42
See application file for complete search history.

(56) References Cited

U.S. PATENT DOCUMENTS

| | | |
|---|---|---|
| 7,576,767 B2 | 8/2009 | Lee et al. |
| 2007/0171519 A1 | 7/2007 | Wolleschensky |

OTHER PUBLICATIONS

Lothar Schermelleh et al., "Subdiffraction Multicolor Imaging of the Nuclear Periphery with 3D Structured Illumination Microscopy." SCIENCE, vol. 320, Jun. 5, 2008, pp. 1332-1336.
Mats G. L. Gustafsson et al., "Three-Dimensional Resolution Doublin in Wide-Field Fluorescence Microscopy by Structured Illumination," Biophysical Journal, vol. 94. Jun. 2008, pp. 4957-4970.
Nadya Chakrova, Bernd Rieger, Sjoerd Stallinga, "Development of a DMD-based fluorescence microscope", Proc. of SPIE vol. 9330 933008-1.
Dan Dan1, Ming Lei1, et al., "DMD-based LED-illumination Super-resolution and optical sectioning microscopy", Scientific Reports | 3 : 1116 | DOI: 10.1038/srep01116.
Song Zhang, Daniel Van Der Welde, James H. Oliver, "Superfast phase-shifting method for 3-D shape measurement", 26 Optics Express 9684, Apr. 2010 / vol. 18, No. 9.
Galasiu, Ciprian, "International Search Report" PCT/IB2015/056405 dated Apr. 27, 2016.
WIPO, International Preliminary Report on Patentability, dated Feb. 27, 2018, re PCT International Patent Application No. PCT/IB2015/056405.

MEDICAL IMAGING SYSTEM FOR ILLUMINATING TISSUE SAMPLES USING THREE-DIMENSIONAL STRUCTURED ILLUMINATION MICROSCOPY

The specification relates generally to medical imaging systems and methods for minimally invasive therapy and image guided medical procedures, and specifically to a medical imaging system for illuminating tissue samples using three-dimensional structured illumination microscopy in port-based surgery.

It is difficult for three-dimensional scanners to image through a medical port when port-based or corridor-based surgery is performed. In particular, illuminating the sample and simultaneously collecting three-dimensional images is challenging. Furthermore, the scanner resolution varies as working distance changes: the longer working distance, the lower the resolution.

SUMMARY

The present disclosure is generally directed to image guided medical procedures which may or may not use an access port. A port-based surgery approach allows a surgeon, or robotic surgical system, to perform a surgical procedure involving tumor resection in which the residual tumor remaining after is minimized, while also minimizing the trauma to the intact white and grey matter of the brain. Is such procedures, trauma may occur, for example, due to contact with the access port, stress to the brain matter, unintentional impact with surgical devices, and/or accidental resection of healthy tissue.

Furthermore, a medical imaging system is provided in which combining optics are used to combine a first light path of a light modulator producing images to illuminate a tissue sample, and a second light path for collecting resulting images from the tissue sample being illuminated. Hence, one set of zoom optics can be used to illuminate a tissue sample and collect resulting images. In particular, the light modulator is used to form images having different patterns, each of the patterns selected to interact with the tissue sample to generate different depth information in each of respective resulting images. For example, the images can comprise features having different resolutions, such as checkerboard patterns, generally selected so that different depth information is collected from each of the respective resulting images. Furthermore, to address issues regarding working distance, further optics and/or lenses are provided between the image modulator and fee combining optics such that the image plane of the images is adjacent the combining optics.

An aspect of the present specification provides a medical imaging system, comprising: an image sensor; a mirror device; zoom optics; a light modulator; a processor in communication with the light modulator; and collimating optics configured to convey one or more images from the light modulator to the mirror device, the mirror device configured to convey the one or more images to the zoom optics, the zoom optics configured: to convey the one or more images from the mirror device to a tissue sample; and convey one or more resulting images, formed by the one or more images illuminating the tissue sample, back to the mirror device, the mirror device further configured to convey the one or more resulting images from the zoom optics to the image sensor, and, the processor configured to control the light modulator to form the one or more images, the one or more images including at least one pattern selected to interact with the tissue sample to generate different depth information in each of the one or more resulting images.

The one or more images can include at least: a first image having a given first pattern; and a second image comprising a gives second pattern different from the first pattern, each of the first pattern and the second pattern selected to interact with the tissue sample to generate different depth information in each of one or more respective resulting images.

The light modulator can comprise one or more of a DMD (digital micromirror device), and an LCOS (liquid crystal on silicon) device.

The medical imaging system can further comprise a light source configured to illuminate the light modulator to generate the one or more images, the light source comprising one or more of a lamp, an incoherent light source, a laser and a coherent light source.

The imaging sensor can comprise one or more of a CMOS (Complementary metal-oxide-semiconductor) device, a CCD (charge-coupled device), and a GaAs (gallium arsenide) device.

The collimating optics can be further configured to form an image plane adjacent the mirror device.

The collimating optics can comprise at least a first lens and a second lens, each adjustable along an image path of the one or more images to change a size of features in the first pattern and the second pattern.

The zoom optics can be adjustable to change a size of features in the first pattern and the second pattern.

The medical imaging system can further comprise an objective lens at a distal end of the zoom optics, distal the mirror device, the objective lens configured to focus the one or more images onto the tissue sample.

Each of the one or more images and the one or more resulting images can comprise similar sets of wavelengths, and the mirror device comprises a prism having an angle configured to reflect the one or more images to the zoom optics and transmit the one or more resulting images to the image sensor.

Each of the one or more images and the one or more resulting images can comprise different sets of wavelengths, and the mirror device comprises a dichroic mirror configured to reflect the one or more images to the zoom optics and transmit the one or more resulting images to the image sensor.

The image sensor, the mirror device and the zoom optics can be arranged in a first line. The mirror, the collimating optics and the light modulator can be arranged in a second line perpendicular to the first line.

The medical imaging system can be configured to be used in port-base medical procedures.

Another aspect of the specification provides a method comprising: at a medical imaging system comprising: an image sensor; a mirror device; zoom optics; a light modulator; a processor in communication with the light modulator; and collimating optics configured to convey one or more images from the light modulator to the mirror device, the mirror device configured to convey the one or more images to the zoom optics, the zoom optics configured: to convey the one or more images from the mirror device to a tissue sample; and convey one or more resulting images, formed by the one or more images illuminating the tissue sample, hack to the mirror device, the mirror device further configured to convey the one or more resulting images from the zoom optics to the image sensor, controlling, using the processor, the light modulator to form the one or more images, the one or more images including at least one pattern selected to interact with the tissue sample to generate different depth information in each of the one or more resulting images.

Another aspect of the specification provides a computer-readable medium storing a computer program, wherein execution of the computer program is for: at a medical imaging system comprising: an image sensor; a mirror device; zoom optics; a light modulator, a processor in communication with the light modulator; and collimating optics configured to convey one or more images from the light modulator to the mirror device, the mirror device configured to convey the one or more images to the zoom optics, the zoom optics configured: to convey the one or more images from the mirror device to a tissue sample; and convey one or more resulting images, formed by the one or more images illuminating the tissue sample, back to the mirror device, the mirror device further configured to convey the one or more resulting images from the zoom optics to the image sensor, controlling, using the processor, the light modulator to form the one or more images, the one or more images including at least one pattern selected to interact with the tissue sample to generate different depth information in each of the one or more resulting images. The computer-readable medium can comprise a non-transitory computer readable medium.

BRIEF DESCRIPTIONS OF THE DRAWINGS

For a better understanding of the various implementations described herein and to show more clearly how they may be carried into effect, reference will now be made, by way of example only, to the accompanying drawings in which.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of tire present specification.

The systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specifications elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Figure 1:
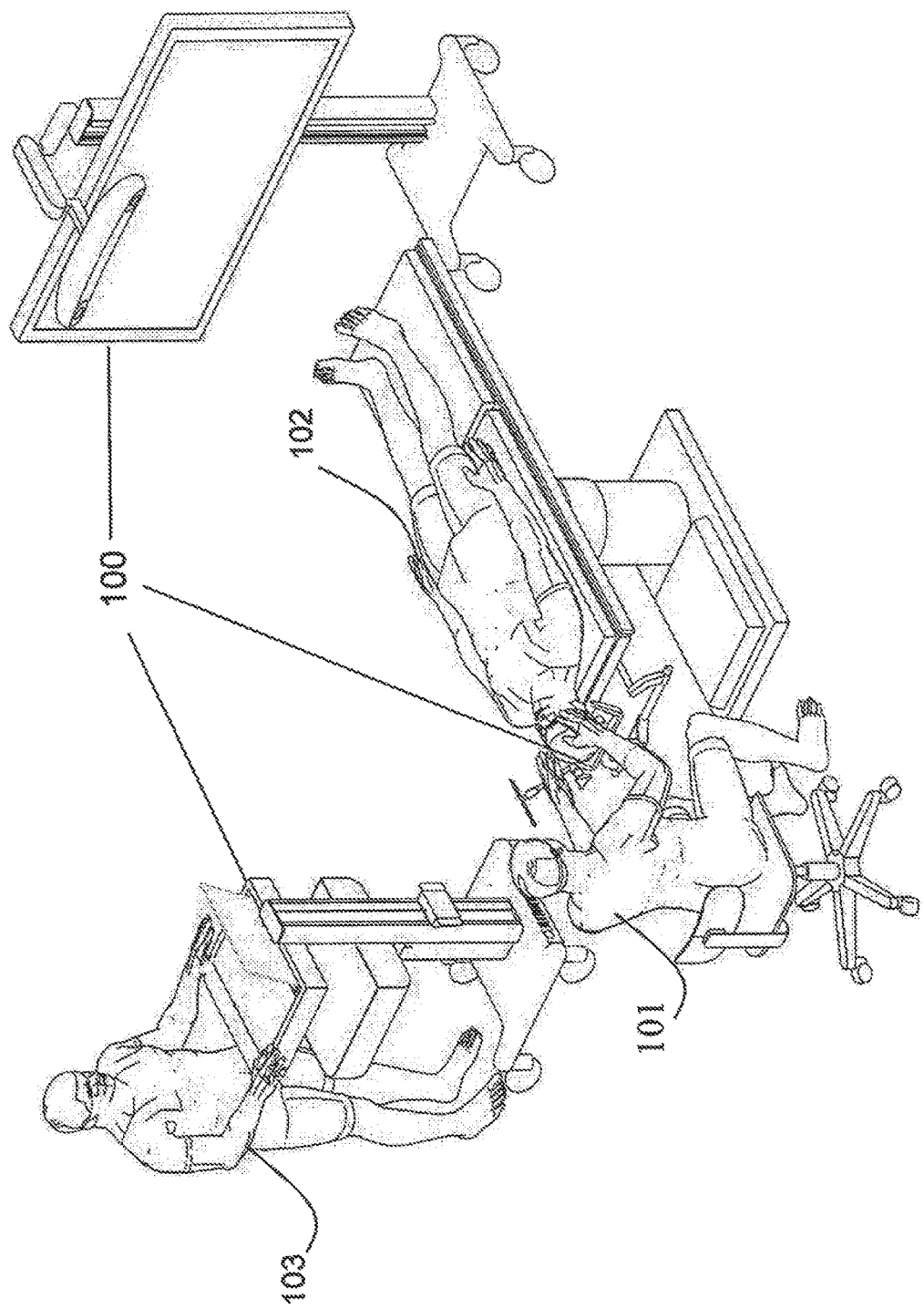
FIG. 1 shows an example operating room setup for a minimally invasive access port-based medical procedure, according to non-limiting implementations.

Referring to FIG. 1, a non-limiting example navigation system 100 is shown to support minimally invasive access port-based surgery or surgical corridor-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
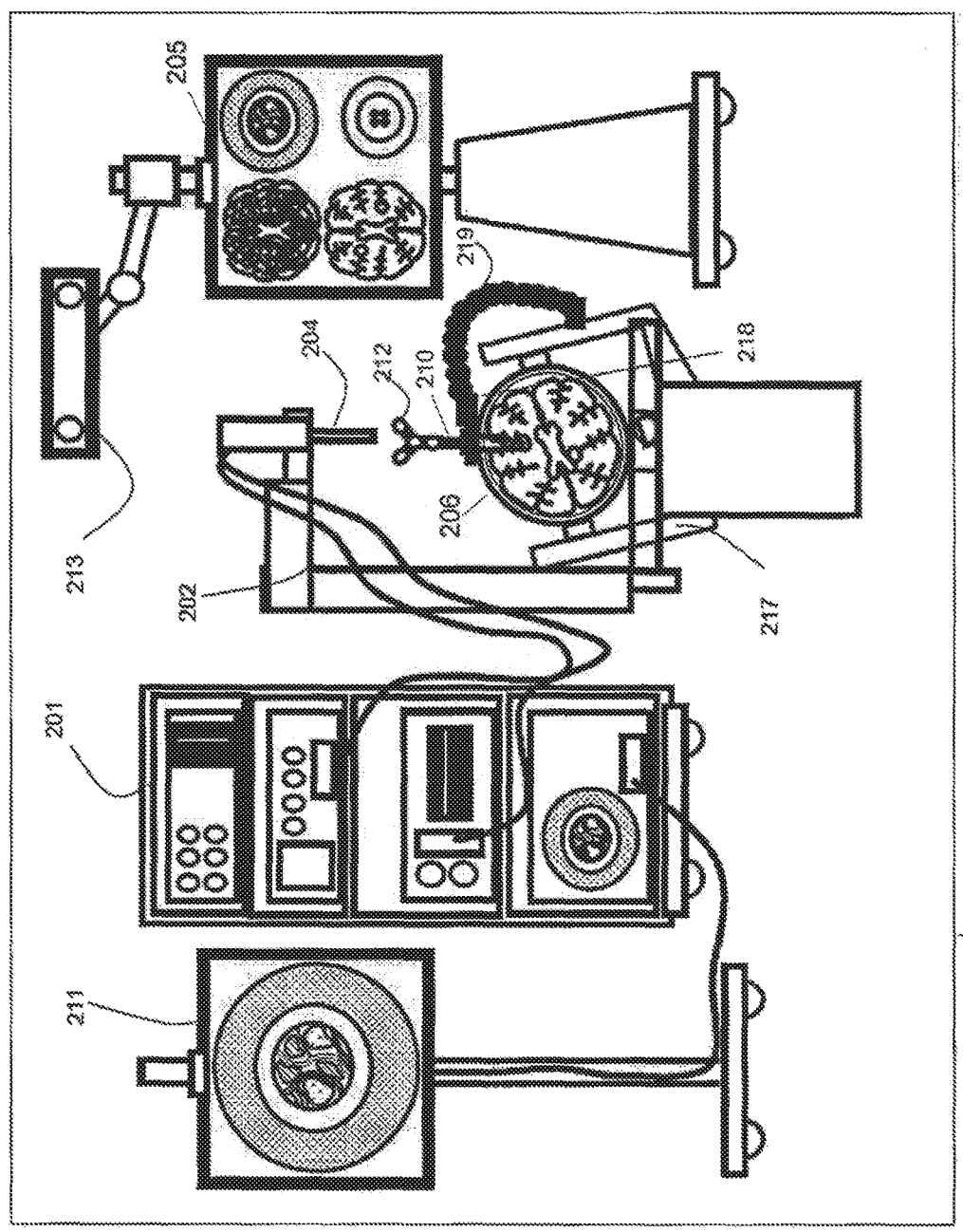
FIG. 2 is a block diagram illustrating components of a medical navigation system that may be used to implement a surgical plan for a minimally invasive surgical procedure, according to non-limiting implementations.

Referring to FIG. 2, a block diagram is shown illustrating components of an example medical navigation system 200, according to non-limiting implementations. The medical navigation system 200 illustrates a context in which a surgical plan including equipment (e.g., tool and material) tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, 205, however other configurations may also exist (e.g., dual tower, single display, etc,). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 232 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal view as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed positions. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support such as on the surgical bed), to ensure that when locked in place, the guide clamp 218 does not move relative to the patient's head.

Figure 3:
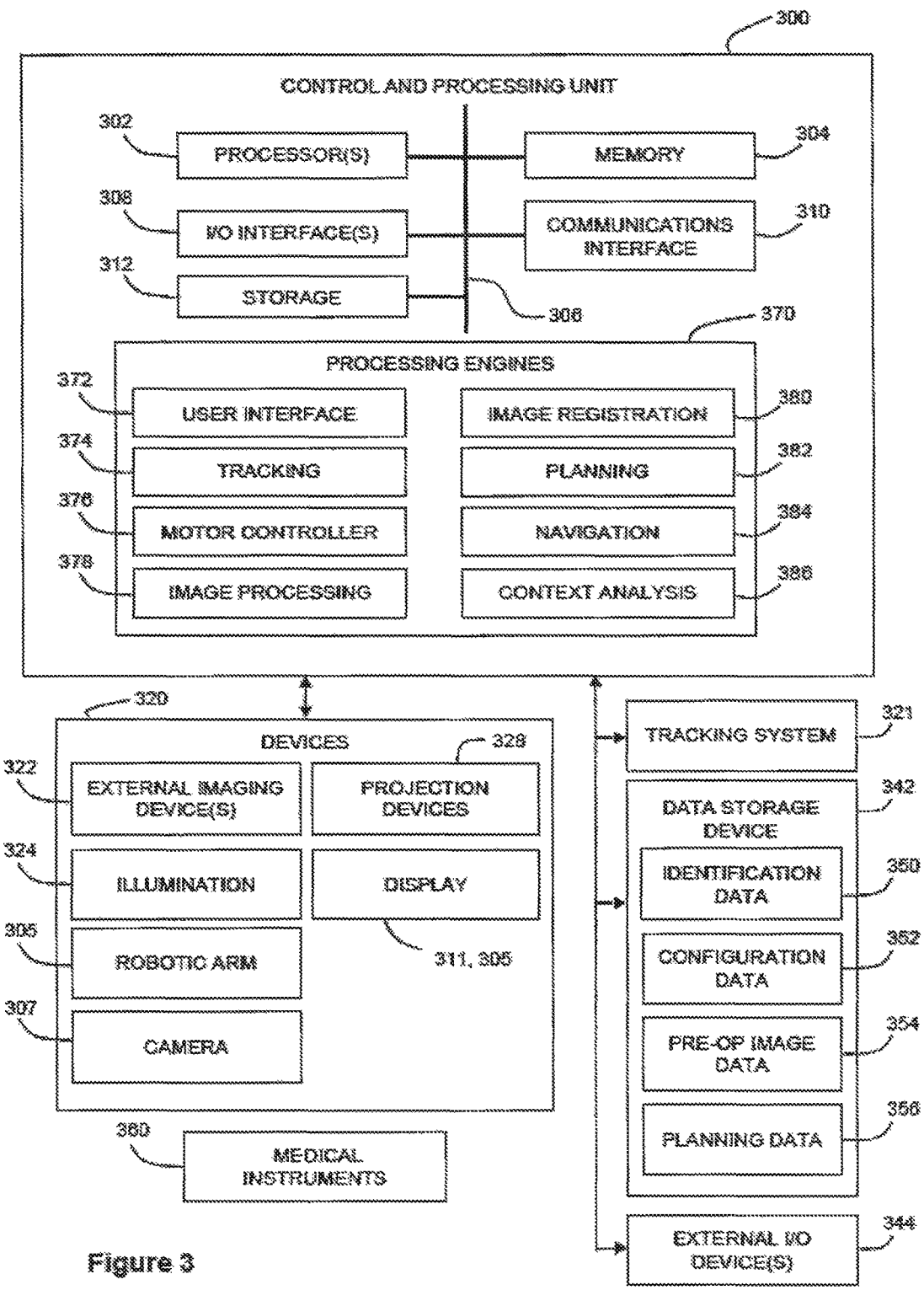
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as past of the equipment tower). In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to as intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually, effect the distribution.

At least some aspects disclosed may be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, non-volatile memory and/or cache. Portions of this software and/or data may be stored in any one of these storage devices.

Examples of computer-readable storage media include, but are not limited to, recordable and non-recordable type media such as volatile and non-volatile memory devices, read-only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium, that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumours and intracranial hemorrhages (ICH), the navigation system 200 may also be applied to a brain biopsy, a functional/deep-brain stimulations a catheter/shunt placement procedure, open craniotomies, endonasal/skull-based/ENT, spine procedures, and other parts of the body such as breast biopsies, liver biopsies, etc. While several examples have been provided, aspects of the present specification may be applied to other suitable medical procedures.

Figure 4:
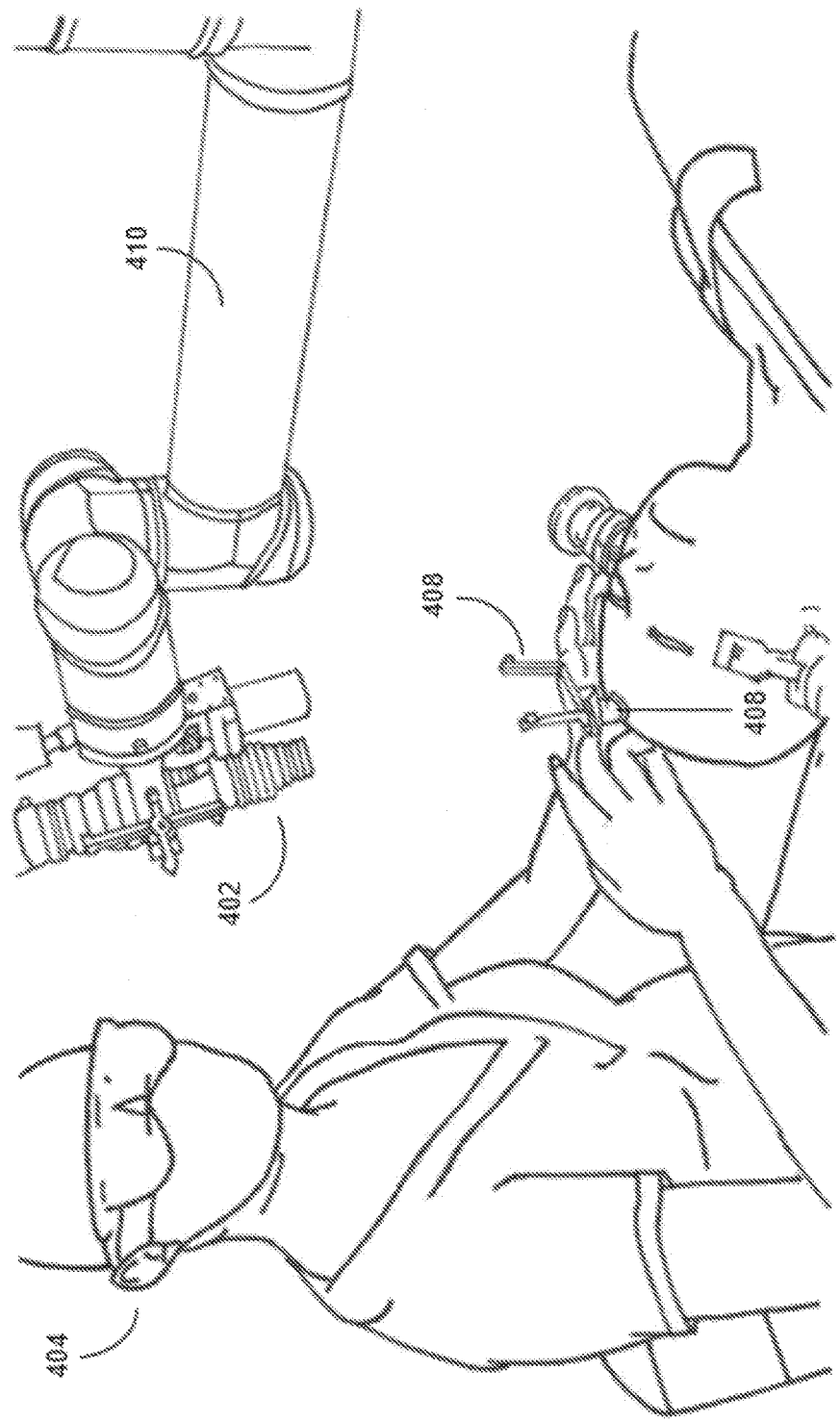
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
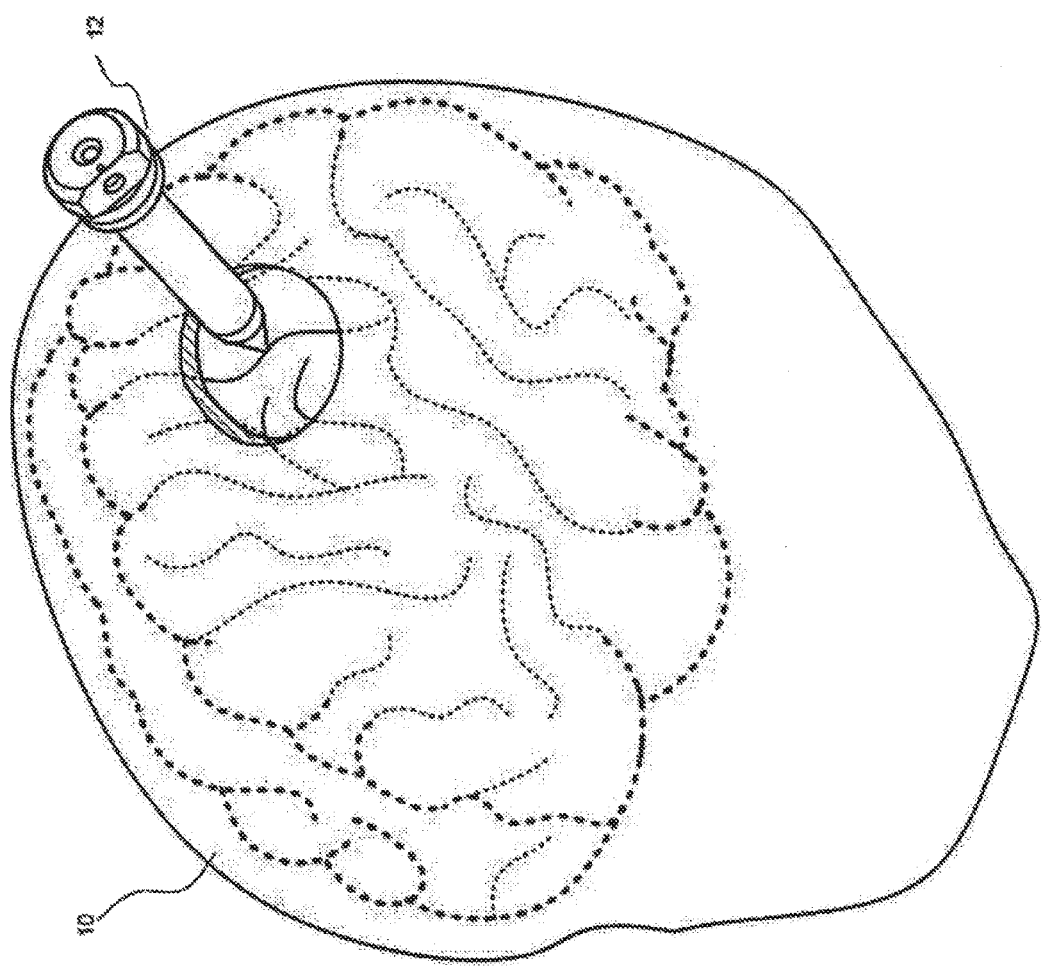
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath™. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments and/or surgical tools would then be inserted down the access port 12.

Figure 6:
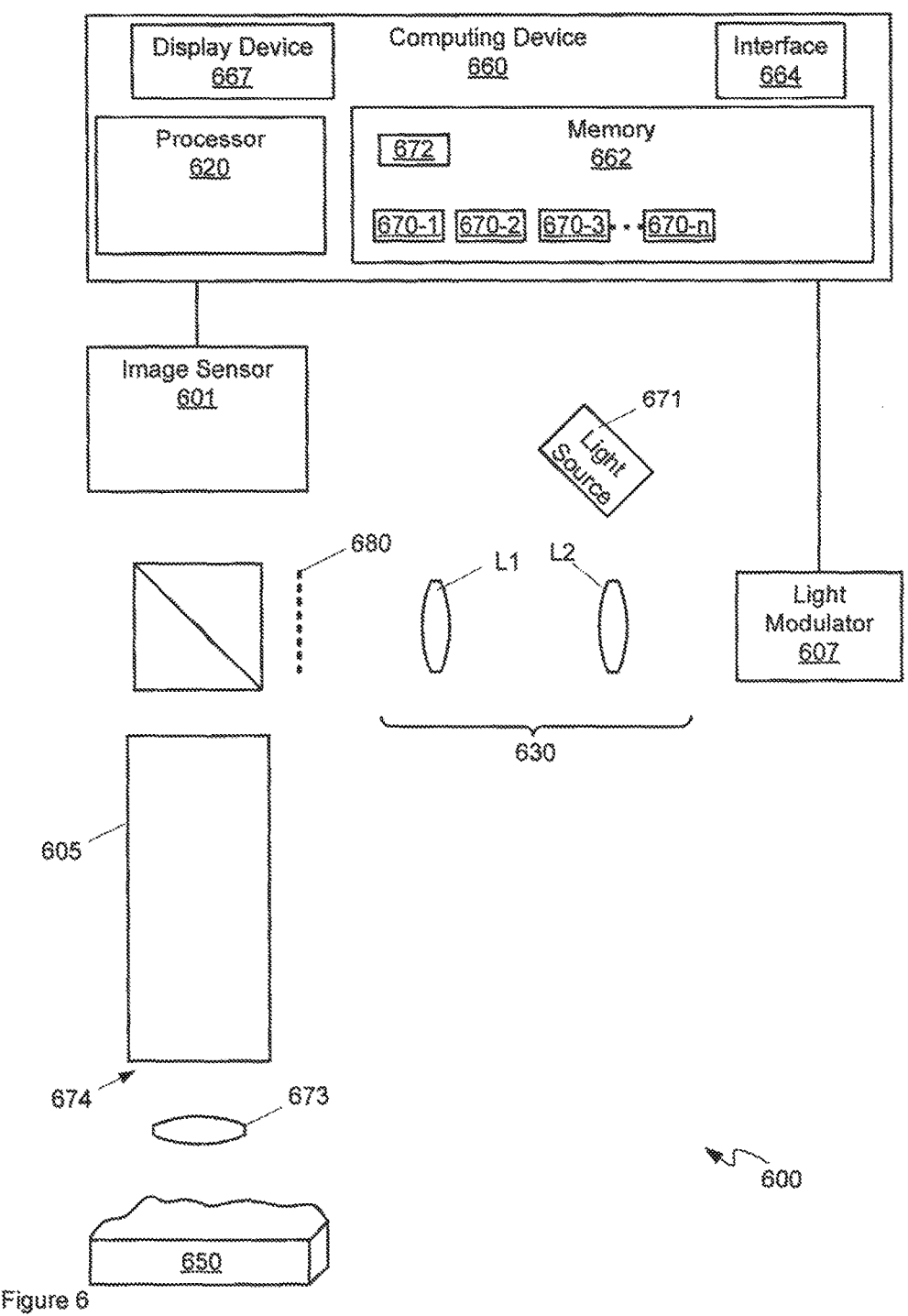
FIG. 6 depicts a medical imaging system for illuminating tissue samples, according to non-limiting implementations.

Attention is next directed to FIG. 6, which depicts an example of a medical imaging system that could be used with and/or in place of access port 12.

In particular, FIG. 6 depicts a medical imaging system 600 comprising: an image sensor 601; a mirror device 603; zoom optics 605; a light modulator 607; a processor 620 in communication with light modulator 607; and collimating optics 630 configured to convey one or more images from light modulator 601 to mirror device 603, mirror device 603 configured to convey the one or more images to zoom optics 605, zoom optics 605 configured: to convey the one or more images from mirror device 603 to a tissue sample 650; and convey resulting images, formed by the one or more images illuminating tissue sample 650, back to mirror device 603, mirror device 603 further configured to convey the resulting images from zoom optics 605 to image sensor 601, and, processor 620 configured to control light modulator 607 to form the one or more images, the one or more images including, the one or more images including at least one pattern selected to interact with the tissue sample 650 to generate different depth information in each of the one or more resulting images. For example, the one or more images can comprise one image comprising one pattern selected to interact with the tissue sample to generate different depth information in resulting images. However, in other implementations, the one or more images can include at least: a first image having a given first pattern; and a second image comprising a given second pattern different from the first pattern, each of the first pattern and the second pattern selected to interact with tissue sample 650 to generate different depth information in each of one or more respective resulting images.

As depicted, system 600 further comprises a computing device 660 comprising processor 620, a memory 662, a communication interface 664 and a display device 667. Memory 662 can further store at least one data file 670-1, 670-2, 670-3, . . . 670-n comprising data defining one or more images and/or patterns selected to interact with tissue samples to generate different depth information when the one or more images and/or patterns illuminate tissue samples. Data files 670-1, 670-2, 670-3 to 670-n will interchangeably be referred to hereafter, collectively, as data files 670 and, generically, as a data file 670. Furthermore, while "n" data files are depicted, in other implementations, only one data file 670 is stored at memory 662.

In general, computing device 660 can comprise any combination of computing devices including, but not limited to, personal computers, graphics devices, laptop devices, medical computing devices and the like. In particular, computing device 660 can comprise any combination of control and processing unit 300, devices 320, and, equipment tower 201. Processor 620 can be implemented as a plurality of processors, including but not limited to one or more central processors (CPUs)). Processor 620 can further comprise one or more hardware processors and/or an ASIC (application-specific integrated circuit) processor. Processor 620 is configured to communicate with a memory 662 which can comprise a non-volatile storage unit (e.g. Erasable Electronic Programmable Read Only Memory ("EEPROM"), Flash Memory) and/or a volatile storage unit (e.g. random access memory ("RAM")).

Programming instructions 672 that implement the functional teachings of computing device 660 and/or system 600 as described herein can be maintained, persistently, in memory 662 and used by processor 620 which makes appropriate utilization of volatile storage during the execution of such programming instructions. Those skilled in the art will now recognize that memory 662 is an example of a computer-readable medium, and in particular a non-transitory computer-readable medium, storing a computer program, wherein execution of the computer program is for configuring the processor 620 as described herein. Furthermore, memory 662 is also an example of a memory unit and/or memory module.

In general, when processor 620 processes such instructions 672 stored at memory 662, processor 620 is configured to: control light modulator 607 to form one or more images from data files 670, the one or more images including at least one pattern selected to interact with the tissue sample 650 to generate different depth information in each of the one or more resulting images. When processor 620 further processes such instructions 672 stored at memory 662, processor 620 is further configured to one or more of: render one or more of resulting images received from image sensor 601 at display device 667; generate one or more three-dimensional images from the one or more resulting images received from image sensor 601; and render one or more three-dimensional images received from image sensor 601 at display device 667.

Interface 664 can the implemented as one or more wired interfaces and wireless interfaces configured to communicate wirelessly and/or using wires with image sensor 601 and light modulator 607.

Display device 667 comprises any suitable one of or combination of CRT (cathode ray tube) and/or flat panel displays (e.g. LCD (liquid crystal display), plasma, OLED (organic light emitting diode), capacitive or resistive touch screens, and the like. Display device 667 can comprise one or more of monitors 205, 211 and displays 305, 311.

As depicted, system 600 further comprises a light source 671 configured to illuminate light modulator 607 to generate one or more images. Light source 671 can include, but is not limited to, one or more of a lamp, an incoherent light source, a coherent light source, a laser and the like.

As depicted, system 600 further comprises an objective lens 673 at a distal end 674 of zoom optics 685, distal mirror device 603, objective lens 673 configured to focus the one or more images onto tissue sample 650.

In particular, collimating optics 630 are configured to form an image plane 680 adjacent mirror device 603. While as depicted collimating optics 630 comprises lenses L1, L2 configured to collimate one or more images from light modulator 607, collimating optics 630 can comprise any combination of optical components configured to form an image plane 680 adjacent mirror device 603, and in particular at an input face of mirror device 603.

Furthermore, as depicted, wherein image sensor 601, mirror device 603 and zoom optics 605 are arranged in a first line. Furthermore, mirror device 603, collimating optics 630 and light modulator 607 are arranged in a second line about perpendicular to the first line. However, any physical configuration of system 600 is within the scope of present implementations where mirror device 603 conveys one or more images from light modulator 607 to zoom optics 605, and conveys resulting images from zoom optics 605 to image sensor 601.

Light modulator 607 comprises one or more of a DMD (digital micromirror device), and an LCOS (liquid crystal on silicon) device. However, any light modulator which can form one or more images from light illuminating light modulator 607 is within the scope of the present implementations.

Light source 671 comprises one or more of a laser device, a light emitting diode (LED) device, an elliptical lamp, and the like, light source 671 generally configured to illuminate light modulator 607 so that light modulator 607 can modulate light from light source 671 into one or more images. For example, light source 671 can include a super-luminance LED (SLED); furthermore, a center wavelength of light source 671 can be in a visible range, according to a human vision system, but can also be in an infrared range, a near-infrared range and the like. In some implementations, a power of light source 671 can be in a range that safe for surgeons, and the like; in such implementations, light source 671 can include, but is not limited to a class I laser.

Indeed, light modulator 607 and light source 671 together with collimating optics 630 and computing device 660, form a projection device configured to project one or more images onto mirror device 603, by forming one or more images at image plane 680.

However, light modulators 607 that include a backlight, and/or are light emitting are also within the scope of present implementations, however, presently, use of a reflecting light modulator and an external light source generally results in brighter images at image plane 680.

Image sensor 601 generally comprises one or more of a camera device, a CMOS (Complementary metal-oxide-semiconductor) device, a CCD (charge-coupled device), and a GaAs (gallium arsenide) device. Image sensor 601 can comprises a high sensitivity sensor (for example relative to consumer-based imaging devices, such as digital cameras) and be further configured to generate a frame of a three-dimensional image. In general, image sensor 601 is configured to receive resulting images that are formed by tissue sample 650 interacting with one or more images received from light modulator 607. As depicted, image sensor 601 is in communication computing device 660 configured to process images captured by image sensor 601 into three-dimensional images.

Operation of system 600 will now be described with reference to FIG. 7 and FIG. 8, each of which is substantially similar to FIG. 6, with like elements having like numbers. In particular, operation of system 600 will be described with reference to two images being formed at light modulator 607, however system 600 can be implemented with as few as one image being formed at light modulator 607, the one image including at least one pattern selected to interact with the tissue sample 650 to generate different depth information in each of the one or more resulting images.

In general, processor 620 and/or computing device 660 is configured to communicate with light modulator 607 to control light modulator 607 to generate one or more images, for example from data files 670. For example, as depicted in FIG. 7, processor 620 sequentially transmits data files 670-1, 670-2 to light modulator 607. Light source 671 produces light 701 which illuminates light modulator 607 while light modulator 607 is being sequentially controlled using data files 670-1, 670-2. Images Im1, Im2 are sequentially formed from light 701 interacting with light modulator 607 while light modulator 607 is being respectively controlled using data files 670-1, 670-2. Images Im1, Im2 are sequentially imaged at image plane 680 using collimating optics 630. Mirror device 603 reflects images Im1, Im2 into zoom optics 605, which conveys images Im1, Im2 through objective lens 673 to tissue sample 650. Each of collimating-optics 630 and zoom optics 605 can magnify images Im1, Im2.

Hence, images Im1, Im2 hence sequentially illuminate tissue sample 650 which hence interact with tissue sample 650 to generate different depth information in each of respective resulting images.

Figure 8:
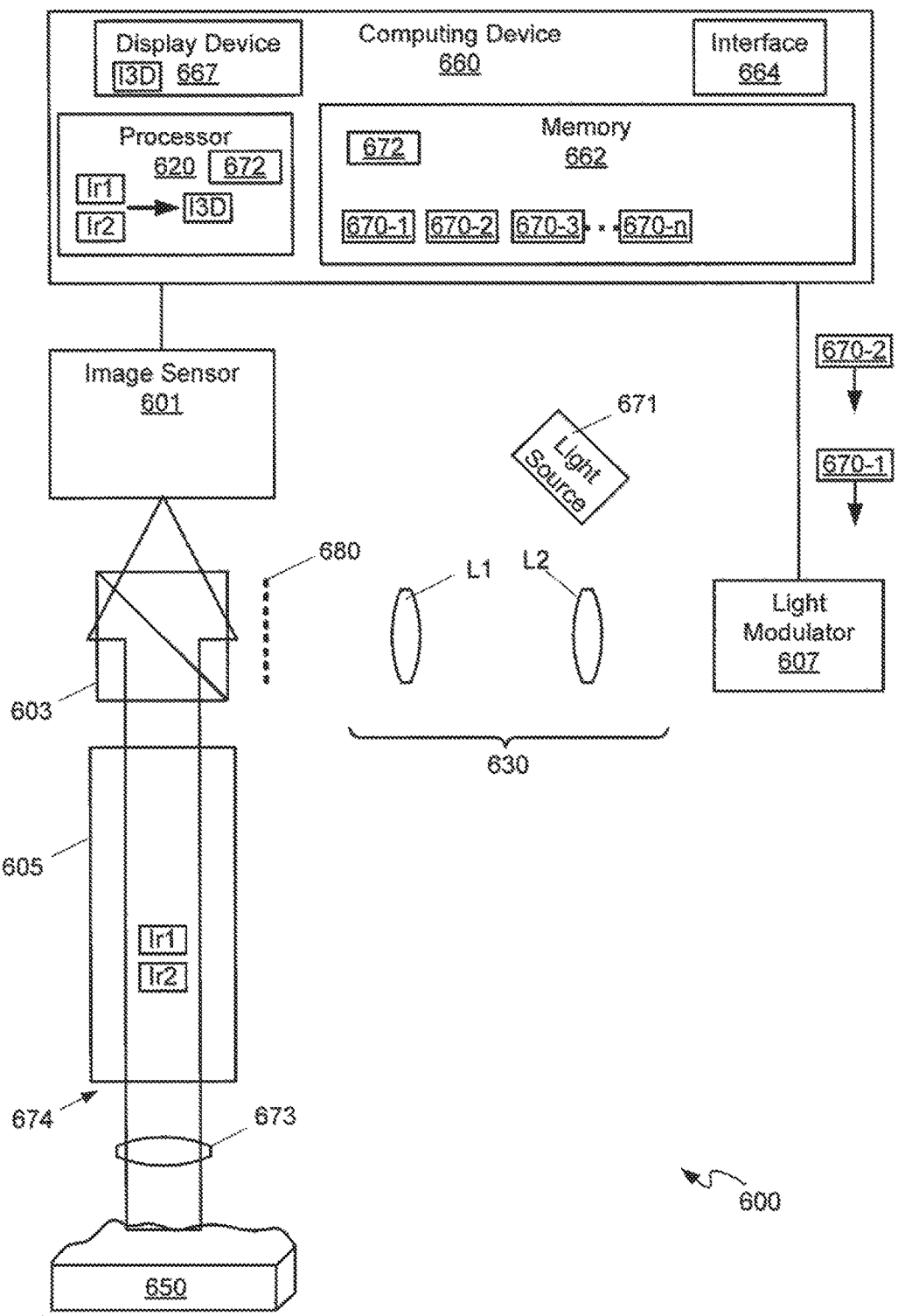
FIG. 8 depicts the system of FIG. 6 conveying images of a tissue sample to an image sensor to produce a three-dimensional image, according to non-limiting implementations.

With reference to FIG. 8, resulting images Ir1, Ir2, respectively formed by image Im1 illuminating tissue sample 650 and image Im2 illuminating tissue sample 650, are conveyed to image sensor 601 via objective lens 673, zoom optics 605 and mirror device 603. However, when one image is used to illuminate tissue sample 650, only one resulting image is conveyed to image sensor 601 via objective lens 673, zoom optics 605 and mirror device 603.

In other words, light (e.g. images Im1, Im2) impinging on mirror device 603 from light modulator 607 is reflected towards zoom optics 605, while light (e.g. images Ir2, Ir2) impinging on mirror device 603 are transmitted through mirror device 603 towards image sensor 601. As such, when each of images Im1, Im2, and resulting images Ir1, Ir2 comprise similar sets of wavelengths, mirror device 603 can comprises a prism having an angle configured to reflect images Im1, Im2 to zoom optics 605 and transmit resulting images Ir1, Ir2 to image sensor 601.

However, in some implementations images (e.g. Images Im1, Im2) conveyed to tissue sample 605, and resulting images (e.g. images Ir1, Ir2) can comprise different sets of wavelengths, for example when tissue sample 650 fluoresces and/or has been treated to fluoresce. In other words, in these implementations one or more images conveyed to tissue sample 605 comprise a different set of wavelengths than the one or more resulting images received from tissue sample 650. In these implementations, mirror device 603 can comprises a dichroic mirror configured to reflect images Im1, Im2 to zoom optics 605 and transmit-resulting images Ir1, Ir2 to image sensor 601.

Hence, in general, mirror device 603 can comprise a wide variety of optical components which can be selected depending on the wavelengths of images Im1, Im2 and resulting images Ir1, Ir2.

Figure 7:
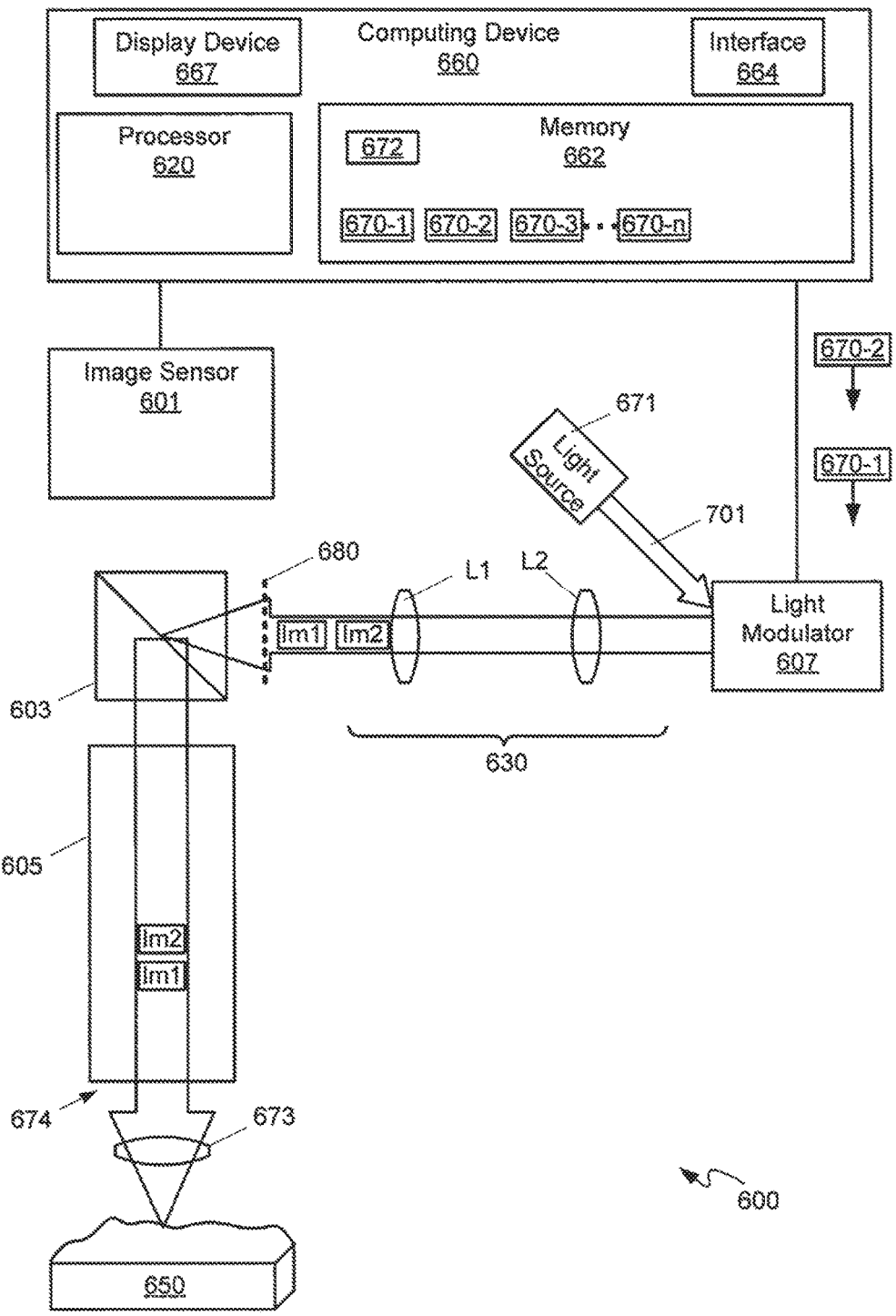
FIG. 7 depicts the system of FIG. 6 illuminating a tissue sample using different light patterns and/or images, according to non-limiting implementations.

It is further appreciated that while conveying of images Im1, Im2 to tissue sample 650, and conveying of resulting images Ir1, Ir2 to image sensor 601 are depicted as being distinct processes in FIG. 7 and in practice such processes occur in tandem; in other words, the processes depicted in FIGS. 7 and 8 occur generally simultaneously and are depicted separately for clarity only.

As described above, processor 620 is generally configured to control light modulator 607 to form one or more images. Specifically, as depicted, images Im1, Im2 include at least: a first image Im1 having a given first pattern; and a second image Im2 having a given second pattern different from the first pattern, each of the first pattern and the second pattern selected to interact with tissue sample 650 to generate different depth information in each of respective resulting images Ir1, Ir2.

Processor 620 and/or computing device 660 is generally feather configured to process one or more resulting images Ir1, Ir2 to produce a three-dimensional image I3D, which can be rendered at display device 667, as also depicted in FIG. 8. For example, processor 620 processes instructions 672 which comprises a decoding algorithm which, when processed, causes processor 620 to calculate multiple frames of three-dimensional image I3D from one or more resulting images Ir1, Ir2 and generates depth information from one or more resulting images Ir1, Ir2. Furthermore, in some implementations, processor 620 can overlay three-dimensional image I3D with visible light image frames. For example, in these implementations, one or more of illuminating images (i.e. conveyed to tissue sample 650 in manner similar to images Im1, Im2) can comprise visible illumination light, that is not formed into a pattern so that image sensor 601 acquires a two-dimensional visible light image frame, which can the combined with three-dimensional image I3D at display device 667.

In general, the one or more images that are formed at light modulator 607 include one or more patterns that are selected to interact with tissue sample 650 to generate different depth information in each of the one or more resulting images. For example, the one or more images can include a pattern of dote, and the like which are focused onto image plane 680, which is in turn conveyed to tissue sample 650 as described above. As portions of tissue sample 680 are at different distances relative to image plane 680 (e.g. tissue sample 650 has an irregular surface with different depths), some of the dots in the resulting image will be in focus, for example those where the height of tissue sample 650 corresponds to a focal plane of objective lens 673, and some of the dots will be out of focus. A degree of focus of corresponding dots in the resulting image, and/or degree of blur of corresponding dots in the resulting image and/or a size of corresponding dots in the resulting image can indicate a depth of tissue sample 650 at the location of the dot.

Furthermore, zoom optics 605 can generally comprise at least one focus module that can include, but is not limited to, one or more of: a motorized control focus module, an adaptive optics focus module, such as acoustic lens, and the like. The at least one focus module can be generally configured to adjust a focus plane of images projected onto tissue sample 650 by scanning; such scanning can generally calibrate system 600 by calculating depth information. For example, a calibration can be performed in which a known pattern is projected onto a known sample, including, but not limited to, a known calibration sample with known heights and/or depths. The one or more focus modules can be used to project the known image onto the sample at different focal planes, and the blur in the resulting images can be analyzed and stored, for example as blur calibration data. In particular, different blurring patterns can be recognized and associated with depth information. Hence, different directions of depth can be calibrated and used for decoding depth information in using blurring in images received at image sensor 601 when images are projected onto a tissue sample. For example, in-focus portions of projected images, and out-of-focus portions of projected images (e.g. images Ir1, Ir2 that result when images Im1, Im2 are projected onto tissue sample 650) can be used to determine depth information using the blur calibration data.

Alternatively, the one or more images projected onto tissue sample 650 can comprise a Moiré pattern and depth information can be extracted from the resulting images. In further implementations, the one or mote images projected onto tissue sample 650 can comprise different wavelengths, and depth information can be extracted from the resulting images. In addition, the one or more images projected onto tissue sample 650 can comprise coherent light (for example, when light source 671 comprises a coherent light source) or incoherent light (for example, when light source 671 comprises an incoherent light source). Further, when two or more images are projected onto tissue sample 650, the images can be the same, but shifted by given amounts; for example an image with a pattern of dots can be projected at least twice, but shifted by a given amount.

Indeed, in general, any pattern from 3D structured illumination microscopy ("SIM") can be used with implementations described herein.

Furthermore, while two patterns and/or images Im1, Im2 are depicted as being projected onto tissue sample 650, in other implementations, more than two patterns and/or images can be projected onto tissue sample 650, for example, one for each data file 670. Alternatively, patterns and/or images to project onto tissue sample 650 can be generated dynamically.

Furthermore, when changing a light pattern from image Im1 to image Im2, whether using data files 670 and/or dynamically, phase information can be embedded into the light patterns and hence also embedded into images Ir1, Ir2 received at image sensor 601. Processor 620 is hence generally configured to process images Ir1, Ir2 to extract depth information. Indeed, while only two patterns are depicted, more than two patterns (i.e. more than two illuminating images) can be used to generate a point cloud in a data set of a three-dimensional image. In general, the more patterns and/or the more illuminating images of different patterns, the more data points are processed and the higher the resolution of a resulting three-dimensional image.

Furthermore, as described above, collimating optics 630 comprise at least a first lens L1 and a second lens L1, and each of first lens L1 and second lens L1 can be adjustable along an image path of images Im1, Im2 to change a size of features in the first pattern and the second pattern. For example, an image path in system 600 can comprise the line formed by light modulator 607, lenses L1, L2, and mirror device 603, and lenses L1. L2 can be adjustable along such a line.

Similarly, zoom optics 605 can be adjustable to change a size of features in the first pattern and the second pattern of images Im1, Im2.

Hence, a respective magnification of both collimating optics 630 and zoom optics 605 can be combined and/or a respective magnification of collimating optics 630 is multiplied by a respective magnification of zoom optics 605. As such, a resolution of a light pattern of one or more of images Im1, Im2 can be very fine and/or comprises a high resolution, and the resolution of a light pattern can be controlled by controlling collimating optics 630 and/or zoom optics 605. Such an adaptive resolution directly can contributes to imaging quality and can generally improve the three-dimensional vision resolution.

System 600 can be further configured to acquire the depth information from imaging including fluorescence imaging and wide-field imaging, however in each instance algorithm that determine depth information can be different. For example, when system 600 is operated in a fluorescence imaging mode, algorithms based on interfering coherent light beams can be used, and system 600 is adapted accordingly. Furthermore, when system 600 is operated in a wide field imaging mode, one or more of the processes described above can be used (e.g. using blurring calibration data) and/or other processes that will occur to persons of skill in the art.

Figure 9:
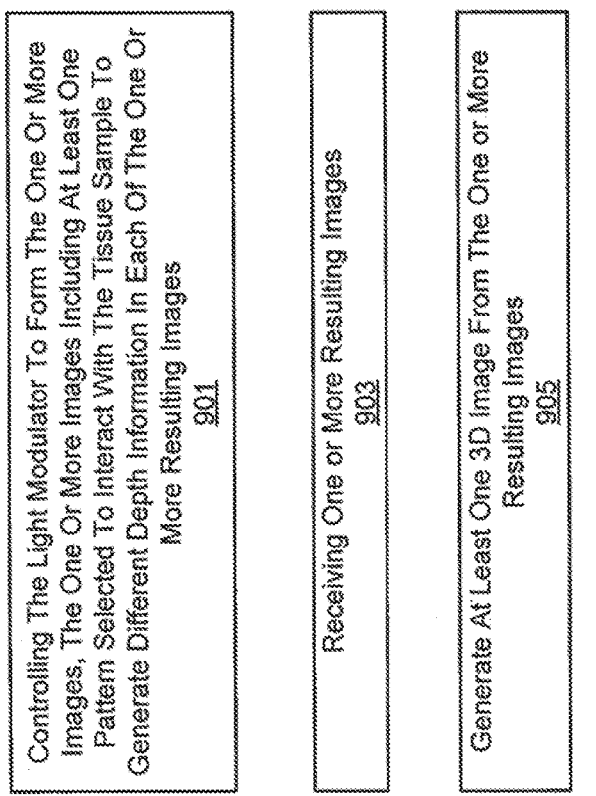
FIG. 9 depicts a block diagram of a flowchart of a method for generating a three-dimensional image.

Attention is now directed to FIG. 9 which depicts a block diagram of a flowchart of a method 900 for generating a 3D image, according to non-limiting implementations. In order to assist in the explanation of method 900, it will be assumed that method 900 is performed using computing device 660, and specifically by processor 620 and when processor 620 processes instructions stored at memory 662. Indeed, method 900 is one way in which computing device 660 can be configured. Furthermore, the following discussion of method 900 will lead to a further understanding of computing device 660, system 600, and its various components. However, it is to be understood that computing device 660 and/or method 900 can be varied, and need not work exactly as discussed herein in conjunction with each other, and that such variations are within the scope of present implementations.

Regardless, it is to be emphasized, that method 900 need not be performed in the exact sequence as shown, unless otherwise indicated; and likewise various blocks may be performed in parallel rather than in sequence; hence the elements of method 900 are referred to herein as "blocks" rather than "steps". It is also to be understood, however, that method 900 can be implemented on variations of computing device 660 as well.

At block 901, processor 620 controls light modulator 607 to form the one or more images, the one or more images including at least one pattern selected to interact with the tissue sample 650 to generate different depth information in each of the one or more resulting images; At block 903, processor 620 receives the resulting images, as described above. At block 905, processor 620 generates one or more 3D images from the resulting images. It is assumed in method 900 that the images projected onto tissue sample 950 are projected in the same image plane, and the images conveyed to the tissue sample 650 and the resulting images received from the tissue sample 650 travel through the same zoom optics 605, as described above. Furthermore, the once the one or more 3D images are generated the one or more 3D images can be rendered at display device 667 and the like, for example to present the one or more displays 305, 311 to a surgeon (e.g. when tissue sample 650 is an in-vivo tissue sample that is being operated on by the surgeon).

Provided herein is a medical imaging system that includes components that can project patterns and/or images onto a tissue sample, where common path optics are at least partially shared between the patterns and/or images being projected onto a field of view and the resulting images collected from the field of view by an image sensor.

The medical imaging system can be specifically used with port-base surgery, for example with the component depicted in FIGS. 4 and 5. Prior art three-dimensional scanners used with port-based surgery generally have comparatively small fields of view, and make it difficult to see through the port; they can also generally require multi positioning and/or rotation to increase point cloud density and are hence very complicated. In contrast, the presently disclosed medical imaging system simplifies system design as compared to prior art three-dimensional scanners as there is so need to rotate any component, and hence no mechanical steering. Furthermore, because of the shared optical path, coaxial illumination can be used to project the patterns and/or images through a port.

Furthermore, in presently disclosed medical imaging system resulting images can be decoded and rendered at a display device with depth information, for example by adding and/or overlaying three-dimensional information onto two-dimensional images.

In addition, the resolution of the light patterns and/or illuminating images disclosed herein can the controlled by the system configuration, for example by controlling the collimating optics and/or the zoom optics. Indeed, as the collimating optics both collimate and magnify the illuminating images, a total magnification is obtained from the combination of respective magnifications of the collimating optics and the zoom optics . . . . For example, when the zoom optics are set at a relatively low magnification, and the light modulator comprises a DMD, the image of single micromirror (light pattern) can be projected on a surface of a tissue sample by controlling the magnification of the collimating optics, and hence the pattern and/or illuminating image can be controlled to a relatively high resolution. A similar procedure can be used to control the resolution by controlling the magnification of the zoom optics. Such adaptive resolution can contributes to improving the three-dimensional resolution of the presently disclosed medical imaging system.

While features of medical imaging systems described with reference to specific implementations, features described wife reference to one implementation of a medical imaging systems may be used with other implementations of medical imaging systems. For example, any of the medical imaging systems described herein may be adapted to include anti-reflective coatings, immersion materials, index matching materials, tracking devices, and the like.

The specific embodiments described above have been, shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A medical imaging system, comprising:
an image sensor; a mirror device; zoom optics; a light modulator; a processor in communication with the light modulator; and collimating optics configured to convey one or more images from the light modulator to the mirror device,
the mirror device configured to convey the one or more images to the zoom optics,
the zoom optics configured: to convey the one or more images from the mirror device to a tissue sample; and convey one or more resulting images, formed by the one or more images illuminating the tissue sample, back to the mirror device,
the mirror device further configured to convey the one or more resulting images from the zoom optics to the image sensor, and,
the processor configured to control the light modulator to form the one or more images, the one or more images including at least one pattern selected to interact with the tissue sample to generate different depth information in each of the one or more resulting images.

2. The medical imaging system of claim 1, wherein the one or more images include at least: a first image having a given first pattern; and a second image comprising a given second pattern different from the first pattern, each of the first pattern and the second pattern selected to interact with the tissue sample to generate different depth information in each of one or more respective resulting images.

3. The medical imaging system of claim 1, wherein the light modulator comprises one or more of a DMD (digital micromirror device), and an LCOS (liquid crystal on silicon) device.

4. The medical imaging system of claim 1, further comprising a light source configured to illuminate the light modulator to generate the one or more images, the light source comprising one or more of a lamp, an incoherent light source, a laser and a coherent light source.

5. The medical imaging system of claim 1, wherein the imaging sensor comprises one or more of a CMOS (Complementary metal-oxide-semiconductor) device, a CCD (charge-coupled device), and a GaAs (gallium arsenide) device.

6. The medical imaging system of claim 1, wherein the collimating optics are further configured to form an image plane adjacent the mirror device.

7. The medical imaging system of claim 1, wherein the collimating optics comprise at least a first lens and a second lens, each adjustable along an image path of the one or more images to change a size of features in the first pattern and the second pattern.

8. The medical imaging system of claim 1, wherein the zoom optics are adjustable to change a size of features in the first pattern and the second pattern.

9. The medical imaging system of claim 1, further comprising an objective lens at a distal end of the zoom optics, distal the mirror device, the objective lens configured to focus the one or more images onto the tissue sample.

10. The medical imaging system of claim 1, wherein each of the one or more images and the one or more resulting images comprise similar sets of wavelengths, and the mirror device comprises a prism having an angle configured to reflect the one or more images to the zoom optics and transmit the one or more resulting images to the image sensor.

11. The medical imaging system of claim 1, wherein each of the one or more images and the one or more resulting images comprise different sets of wavelengths, and the mirror device comprises a dichroic mirror configured to reflect the one or more images to the zoom optics and transmit the one or more resulting images to the image sensor.

12. The medical imaging system of claim 1, wherein the image sensor, the mirror device and the zoom optics are arranged in a first line.

13. The medical imaging system of claim 12, wherein the mirror, the collimating optics and the light modulator are arranged in a second line perpendicular to the first line.

14. The medical imaging system of claim 1 wherein the medical imaging system is configured to be used in port-base medical procedures.

15. A method comprising:
at a medical imaging system comprising: an image sensor; a mirror device; zoom optics; a light modulator; a processor in communication with the light modulator; and collimating optics configured to convey one or more images from the light modulator to the mirror device, the mirror device configured to convey the one or more images to the zoom optics, the zoom optics configured: to convey the one or more images from the mirror device to a tissue sample; and convey one or more resulting images, formed by the one or more images illuminating the tissue sample, back to the mirror device, the mirror device further configured to convey the one or more resulting images from the zoom optics to the image sensor, controlling, using the processor, the light modulator to form the one or more images, the one or more images including at least one pattern selected to interact with the tissue sample to generate different depth information in each of the one or more resulting images.

16. A non-transitory computer-readable medium storing a computer program, wherein execution of the computer program is for:
at a medical imaging system comprising: an image sensor; a mirror device; zoom optics; a light modulator; a processor in communication with the light modulator; and collimating optics configured to convey one or more images from the light modulator to the mirror device, the mirror device configured to convey the one or more images to the zoom optics, the zoom optics configured: to convey the one or more images from the mirror device to a tissue sample; and convey one or more resulting images, formed by the one or more images illuminating the tissue sample, back to the mirror device, the mirror device further configured to convey the one or more resulting images from the zoom optics to the image sensor, controlling, using the processor, the light modulator to form the one or more images, the one or more images including at least one pattern selected to interact with the tissue sample to generate different depth information in each of the one or more resulting images.

* * * * *